United States Patent [19]
Miyagawa et al.

[11] Patent Number: 5,526,118
[45] Date of Patent: Jun. 11, 1996

[54] APPARATUS FOR OBTAINING REFRACTIVE INDEX DISTRIBUTION INFORMATION OF LIGHT SCATTERING MEDIA

[75] Inventors: Ichirou Miyagawa; Masahiro Toida, both of Kanagawa-ken, Japan

[73] Assignee: Fuji Photo Film Co., Ltd., Kanagawa, Japan

[21] Appl. No.: 350,471

[22] Filed: Dec. 7, 1994

[30] Foreign Application Priority Data

Dec. 7, 1993 [JP] Japan ................................ 5-306341

[51] Int. Cl.⁶ ........................................ G01B 9/02
[52] U.S. Cl. ........................................ 356/361; 356/349
[58] Field of Search ................................ 356/345, 361, 356/349

[56] References Cited

U.S. PATENT DOCUMENTS

| | | | |
|---|---|---|---|
| 4,759,628 | 7/1988 | Tatsuno et al. | 356/349 |
| 5,151,752 | 9/1992 | Oono et al. | 356/361 |
| 5,321,501 | 6/1994 | Swanson et al. | 356/345 |

FOREIGN PATENT DOCUMENTS

| | | | |
|---|---|---|---|
| 63-179223 | 7/1988 | Japan | G01J 3/08 |
| 2110346 | 4/1990 | Japan | G01N 21/27 |
| 2110345 | 4/1990 | Japan | G01N 21/27 |

*Primary Examiner*—Frank Gonzalez
*Assistant Examiner*—Robert Kim
*Attorney, Agent, or Firm*—Sughrue, Mion, Zinn, Macpeak & Seas

[57] ABSTRACT

A superheterodyne split-beam system is used to measure the refractive index distribution associated with a light scattering medium. Initially, a coherent light beam is split into a first reference light beam and a second light beam. The second light beam is passed through a light scattering medium. Scattered and unscattered portions of the second light beam are separated using the characteristic that the scattered light travels by a longer optical path length than the unscattered light. The first light beam is recombined with the unscattered light beam, and the associated optical path difference is measured. Using the difference between the calculated path difference and a predetermined reference path difference, as well as the thickness of the scattering medium, refractive indices are measured. The use of a photodetector array allows for determining a distribution of the refractive indexes of the inclusions at various portions of the medium.

10 Claims, 9 Drawing Sheets

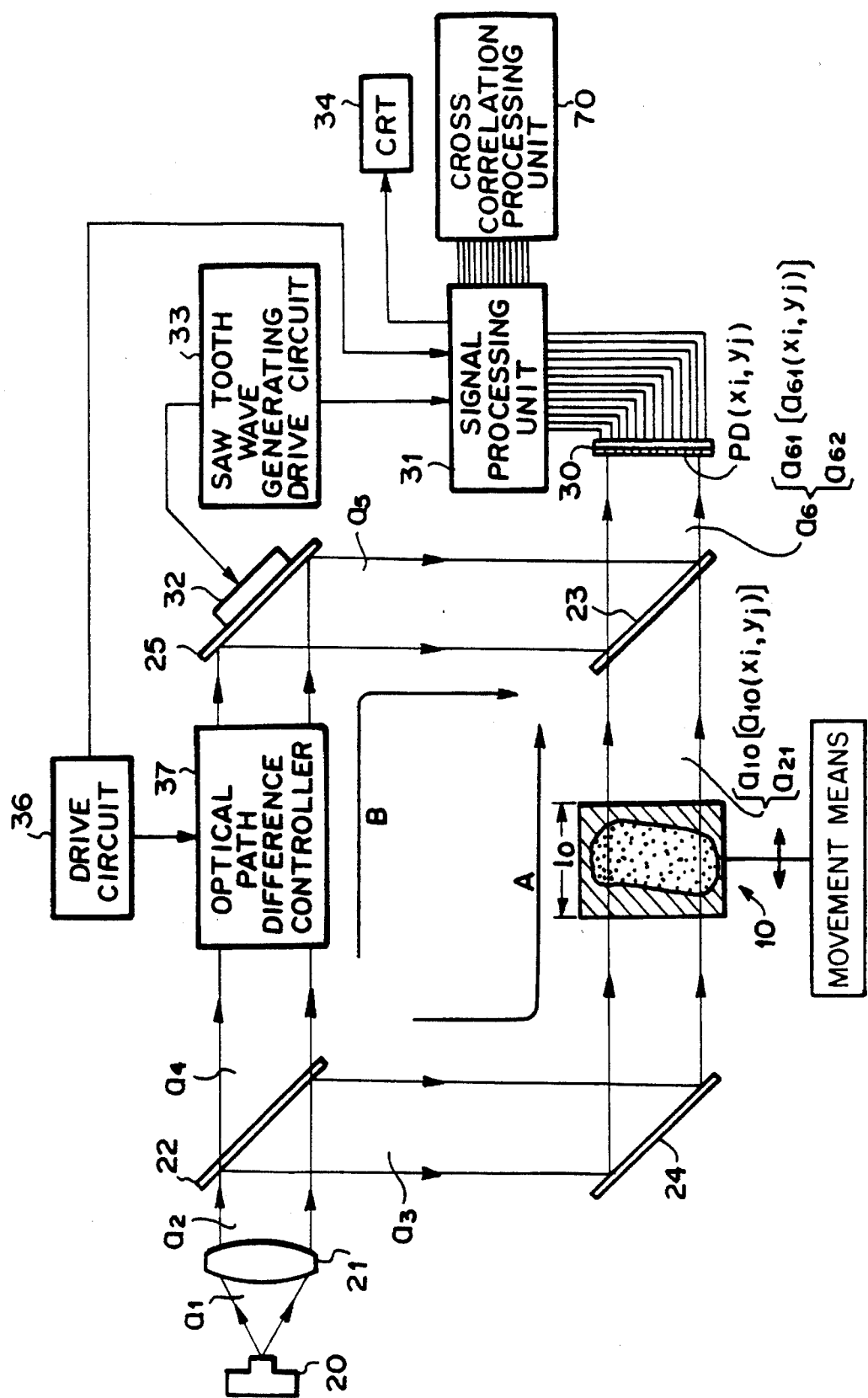

APPARATUS FOR OBTAINING REFRACTIVE INDEX DISTRIBUTION INFORMATION OF LIGHT SCATTERING MEDIA

BACKGROUND OF THE INVENTION

FIELD OF THE INVENTION

This invention relates to an apparatus for obtaining refractive index distribution information of a medium having light scattering properties. This invention particularly relates to an apparatus for obtaining the information representing the distribution of refractive indexes (medium densities) in a region inside of a medium, which has light scattering properties, by utilizing an optical heterodyne detection technique.

DESCRIPTION OF THE PRIOR ART

Various apparatuses have heretofore been used in order to obtain the information representing the forms and/or structures in regions inside of media having light scattering properties. For example, as one of apparatuses for obtaining the information representing the forms and/or structures of inclusions, which are interspersed in the region inside of a medium having light scattering properties, by utilizing the differences in the refractive indexes of the inclusions with respect to light, an apparatus for carrying out an extremely short pulse time gate method has been proposed in, for example, Japanese unexamined Patent Publication No. 63(1988)-179223. The proposed apparatus is provided with a light source for producing pulsed light with a timing, controlled by a timing control device, and a photodetector for irradiating the pulsed light, produced by the light source, to a medium, whose light scattering properties are to be obtained, and detecting the pulsed light, which has passed through the medium having light scattering properties. The proposed apparatus is further provided with a high-speed shutter, which is located between the medium having light scattering properties and the photodetector. In accordance with the control operation of the timing control device, the high-speed shutter can take an open position that allows the light, which has passed through the medium having light scattering properties, to impinge upon the photodetector can also take a closed position that blocks the light which has passed through the medium having light scattering properties. In the proposed apparatus the time required for the pulsed light to pass through the medium having light scattering properties may vary in accordance with the refractive indexes of the inclusions, which are interspersed in the region inside of the medium having light scattering properties, with respect to the light. The opening and closing operation of the high-seed shutter is controlled by utilizing such characteristics, and the light, which has passed through the medium having light scattering properties and which corresponds to the refractive indexes of the inclusions with respect to the light, is obtained selectively.

Also, as the methods for detecting a light beam, passed through a medium having light scattering properties, such as a living body, without being scattered, include optical heterodyne detection methods, as proposed, for example, in Japanese Unexamined Patent Publication Nos. 2(1990)-110345 and 2(1990)110346. With the optical heterodyne detection technique, two light beams having slightly different wavelengths are superposed one upon the other such that their directions of travel may coincide with each other, and the interference of the two light beams occurring due to the difference between their wavelengths is utilized. Only when the directions of travel of the two light beams superposed one upon the other perfectly coincide with each other, a beat signal having an intensity that repeatedly becomes high and low can be detected in a plane, which is normal to the light beams. Therefore, only the light beam which has passed through the medium having light scattering properties without being scattered, can be discriminated very accurately. Also, with optical heterodyne detection techniques having good direction discriminating performance, the difference (i.e., the phase difference) between the phase of the beat signal detected from the light, which has passed through an inclusion in the region inside of the medium having light scattering properties, and the phase of predetermined light taken as a reference corresponds the refractive index difference of the inclusion. Therefore, the refractive index difference of the inclusion can be obtained by carrying out calculation processing on the phase difference.

However with the extremely short pulse time gate method, such that only the desired light which has passed through the medium having light scattering properties, can be selected accurately, it is necessary to use an expensive streak camera as the high-speed shutter. Therefore, the cost of the apparatus for carrying out the extremely short pulse time gate method cannot be kept low. Also, the inclusions are interspersed in the region inside of the medium having light scattering properties. Therefore, in order to obtain the information representing the distribution of the inclusions, it is necessary to carry out the measurement for every point in the medium having light scattering properties. Accordingly, the problems occur in that the measurement time cannot be kept short.

With the optical heterodyne detection technique for obtaining a refractive index difference from the phase difference of the beat signal of the interference wave, the refractive index difference corresponding to an optical path difference on the wavelength order can be obtained accurately. However, with the optical heterodyne detection technique, it is not possible to measure a large refractive index difference corresponding to an optical path difference larger than the wavelength order. Also, of the scattered light, which is scattered many times in the region inside of the medium having light scattering properties and is radiated from the surface of the medium towards various directions, the scattered light (i.e., cross talk light), which is directed to the same travel direction as the light beam, which has passed through the medium without being scattered, becomes mixed into the light beam, which has passed through the medium without being scattered. Therefore, the photodetector detects the light beam, which has passed through the medium without being scattered into which the scattered light has been mixed. As a result, the problems occur in that the signal-to-noise ratio of the detection signal cannot be kept high.

SUMMARY OF THE INVENTION

The primary object of the present invention is to provide an apparatus for obtaining refractive index distribution information of a medium having light scattering properties, wherein a light beam, which has passed through the light scattering medium without being scattered, and scattered light, which is radiated out of the light scattering medium, are perfectly separated from each other, and only the light beam which has passed through the light scattering medium without being scattered, is thereby detected with a high signal-to-noise ratio.

Another object of the present invention is to provide an apparatus for obtaining refractive index distribution information of a light scattering medium, wherein the distribution of large refractive index differences corresponding to optical path differences larger than the wavelength order is measured quickly.

An apparatus for obtaining refractive index distribution information of a light scattering medium in accordance with the present invention is characterized by discriminating a light beam, which has passed through the light scattering medium without being scattered, from scattered light. The scattered light, which is radiated out of the light scattering medium in the same direction am the direction of travel of the light beam having passed through the light scattering medium without being scattered, may travel along an optical path having a longer optical path length than the optical path length of the light beam, which has passed through the light scattering medium without being scattered, in the region inside of the light scattering medium. A calculation is then made to find the difference between the optical path length and the physical path length of the discriminated light beam which has passed through the light scattering medium without being scattered, in the region inside of the light scattering medium. In this manner, a refractive index difference of an inclusion in the region inside of the light scattering medium is obtained. The light beam, which has passed through each of different portions of the light scattering medium without being scattered, is simultaneously detected by each of the photo detecting devices of a photodetector, and the operations described above are carried out. In this manner, the distribution of the refractive indexes of the inclusions at various portions of the light scattering medium is obtained.

Specifically, the present invention provides a first apparatus for obtaining refractive index distribution information of a light scattering medium, comprising:

i) a light source for producing a low coherence light beam, ii) an optical system for splitting the low coherence light beam, which has been produced by the light source, into two light beams, causing the two light beams to travel respectively along two different optical paths, which have approximately equal optical path lengths, and thereafter combining the two light beams with each other, iii) a frequency shifter, which is located in at least either one of the two optical paths and which shifts the frequency of the light beam traveling along at least either one of the two optical paths such that the frequencies of the two light beams traveling respectively along the two optical paths may be different from each other, iv) an optical path difference modulating means, which is located in at least either one of the two optical paths and which modulates the optical path difference between the two optical paths by modulating the length of at least either one of the two optical paths, v) a photodetector for detecting:
 a) the intensity of a combined light beam obtained from the combination of the light beam, which has passed through a light scattering medium without being scattered, the light scattering medium being located in one of the two optical paths, and the light beam having traveled along the other optical path, the combination being effected by the optical system, and
 b) the intensity of a combined light beam obtained from the combination of scattered light traveling in the same direction as the direction of travel of the light beam, which has passed through the light scattering medium without being scattered, and the light beam having traveled along the other optical path, the combination being effected by the optical system, the photodetector comprising a one-dimensional array or a two-dimensional array of a plurality of photo detecting devices, which are arrayed along a plane that is normal to the direction of travel of the combined light beams, and vi) an operation means for:
 a) detecting an optical path difference between the light beam, which has passed through the light scattering medium without being scattered, and the light beam, which has traveled along the other optical path, before being combined with each other, the detection being made for each of the photo detecting devices of the photodetector and in accordance with the optical intensity having been detected by each photo detecting device with respect to each of values, to which the optical path difference has been modulated by the optical path difference modulating means,
 b) calculating the difference value between the optical optical-path difference, which has been detected for each of the photo detecting devices, and a certain optical path difference serving as a reference,
 c) dividing the thus calculated difference value by the thickness of the light scattering medium, and
 d) thereby calculating a refractive index difference at each of different positions in the light scattering medium.

By way of example, as the low coherence light beam, a light beam, which is produced by a super-luminescent diode (SLD) and has a coherence length falling within the range of 40 μm to 50 μm, or a light beam, which is produced by a light emitting diode (LED) has a coherence length falling within the range of 0 to 20 μm, may be employed. A light beam produced by an SLD has good directivity and should preferably be employed as the low coherence light beam.

The term "frequency shifter" as used herein refers to a means for shifting the frequency. By way of example, a means for temporally sweeping and modulating the phase in a saw tooth-like pattern or a means utilizing an acousto-optic modulator (AOM) may be employed as the frequency shifter.

The present invention also provides a second apparatus for obtaining refractive index distribution information of a light scattering medium, comprising:

i) a light source for producing a coherent light beam, ii) a modulation means for temporally sweeping the frequency of the coherent light beam produced by the light source, iii) an optical system for splitting the coherent light beam, which has been modulated by the modulation means, into two light beams, causing the two light beams to travel respectively along two optical paths having an optical path difference, which has been set in advance, and thereafter combining the two light beams with each other, iv) a photodetector for detecting:
 a) the intensity of a combined light beam obtained from the combination of the light beam, which has passed through a light scattering medium without being scattered, the light scattering medium being located in one of the two optical paths, and the light beam having traveled along the other optical path, the combination being effected by the optical system, and b) the intensity of a combined light beam obtained from the combination of scattered light traveling in the same direction as the direction of travel of the light beam, which has passed through the light scattering medium without being scattered, and the light beam having traveled along the other optical path, the combination being effected by the optical system, the photodetector comprising a one-dimensional array or a two-dimensional array of a plurality of photo detecting devices, which are arrayed along a plane that is normal to the direction of travel of the combined light beams, and v) an operation means for:
  a) detecting an optical optical-path difference between the light beam, which has passed through the light scattering medium without being scattered, and the light beam, which has traveled along the other optical path, before being combined with each other, the detection being made for each of the photo detecting devices of the photodetector and in accordance with the optical intensity having been detected by each photo detecting device,
  b) calculating the difference value between the optical optical-path difference, which has been detected for each of the photo detecting devices, and a certain optical optical-path difference serving as a reference,
  c) dividing the thus calculated difference value by the thickness of the light scattering medium, and
  d) thereby calculating a refractive index difference at each of different positions in the light scattering medium.

The light source for producing the coherent light beam may also serve as the modulation means for temporally sweeping the frequency of the coherent light beam produced by the light source.

If the surface of the light scattering medium, which is located in the optical path, has a curved shape or an uneven shape, the light beam impinging upon the light scattering medium will be refracted at the boundary of the light scattering medium. Also, the light beam, which has passed through the light scattering medium without being scattered, will be refracted at the boundary of the light scattering medium when it is radiated out of the light scattering medium. Therefore, it will often occur that the direction of travel of the light beam impinging upon the light scattering medium and the direction of travel of the light beam, which has passed through the light scattering medium without being scattered, do not coincide with each other. In such cases, the light scattering medium may be covered with a light-permeable medium, which has approximately the same refractive index as the refractive index of the light scattering medium and which has a light entry face and a light radiating lace finished to be normal to the direction of travel of the light beam impinging upon the light scattering medium.

In the first and second apparatuses obtaining refractive index distribution information of a light scattering medium in accordance with the present invention, in cases where a one-dimensional photodetector is used, information representing two-dimensional distribution of refractive indexes can be obtained by utilizing a scanning means for scanning at least either one of the one-dimensional photodetector and the system other than the one-dimensional photodetector in a direction, which is approximately normal to the direction along which the one-dimensional photodetector extends.

Also, the first and second apparatuses for obtaining refractive index distribution information of a light scattering medium in accordance with the resent invention may be provided with a movement means for moving at least either one of the light scattering medium, which is a sample to be measured, and an entire system other than the light scattering medium or part the entire system other than the light scattering medium such that the light beam irradiated to the light scattering medium may be rotated and moved with respect to the light scattering medium. Further, the first and second apparatuses for obtaining refractive index distribution information of a light scattering medium in accordance with the present invention may be provided with an image reconstructing means, which is located at a stage after the operation means and is provided with algorithms of computed tomography (CT) capable of forming a three-dimensional refractive index distribution image from the refractive index distribution information obtained at each position of rotation.

With the first apparatus for obtaining refractive index distribution information of a light scattering medium in accordance with the present invention, the low coherence light beam is produced by the light source, such as an SLD. The low coherence light beam is split by an optical element of the optical system, such as a beam splitter, into a first light beam and a second light beam. The first and second light beams travel respectively along a first optical path and a second optical path, which have approximately equal optical path lengths. The two light beams are thereafter combined with each other by an optical element of the optical system, such as a beam splitter, and are thus caused to interfere with each other.

A frequency shifter is located in one of the two optical paths. The frequency of the light beam traveling along the optical path, in which the frequency shifter is located, is shifted to a frequency slightly different from the frequency of the light beam traveling along the other optical path. The light beam traveling along the optical path, in which the medium having light scattering properties is located, impinges upon the light scattering medium. As a result, a light beam, which has passed through the light scattering medium without being scattered, and scattered light are radiated out of the light scattering medium.

The light beam, which has passed through the light scattering medium without being scattered, carries the refractive index information at the portion of the light scattering medium through which the light beam has passed. This is because the optical path length of the light beam passing through the medium corresponds to the refractive index of the medium through which the light beam passes.

The scattered light is radiated out of the light scattering medium towards indefinite directions regardless of the direction of incidence of the light beam upon the light scattering medium. Part of the scattered light is radiated out of the light scattering medium towards the same direction as the direction of travel of the light beam, which has passed through the light scattering medium without being scattered. (The part of the scattered light will hereinbelow be referred to as the "cross talk light.")

Therefore, in order for the refractive index information of the light scattering medium to be obtained with a high signal-to-noise ratio, it is necessary to separate the light beam, which has passed through the light scattering medium without being scattered, and the cross talk light from each other. How they are separated from each other will be described hereinbelow.

The light beam, which passes through the light scattering medium without being scattered, travels the shortest distance through the light scattering medium in the same direction as the direction of travel of the incident light beam. On the other hand, the cross talk light is scattered at least one time by the light scattering substance in the region inside of the light scattering medium and is then radiated out of the light scattering medium. Therefore, the optical path length, by which the cross talk light travels in the region inside of the light scattering medium, becomes longer than the optical path length, by which the light beam passing through the light scattering medium without being scattered travels in the region inside of the light scattering medium. The coherence length of the light beam produced by the light source is short. Therefore, when the optical path difference between the light beam, which has traveled along one of the two optical paths and has a certain frequency, and the light beam, which has passed through the light scattering medium located in the other optical path without being scattered and has a different frequency, or the cross talk light having the different frequency becomes approximately zero, the two light beams having different frequencies interfere with each other at the optical element, such as a beam splitter. In this manner, a beat signal occurs which has an intensity that repeatedly becomes high and low at a frequency equal to the difference between the frequencies of the two light beams.

The interference light is classified in accordance with the optical path difference between the two optical paths into interference light resulting from the interference of the light beam passed through the light scattering medium without being scattered and the light beam which has traveled along the other optical path, and the interference light resulting from the interference of the cross talk light and the light beam which has traveled along the other optical path.

With the first apparatus for obtaining refractive index distribution information of a light scattering medium in accordance with the present invention, the length of either one of the two optical paths is changed by the optical path difference modulating means. In this manner, the interference light associated with the light beam which has passed through the light scattering medium without being scattered and which has thus traveled along the optically shortest distance, can be discriminated from the interference light associated with the cross talk light, which has traveled along an excessive optical path. The discriminated light beam, which has passed through the light scattering medium without being scattered and which has thus traveled along the optically shortest distance, involves optical path differences in accordance with the refractive index differences at different portions of the light scattering medium. Therefore, a calculation is made to find the difference between the optical path difference at each of different positions in the light scattering medium and the optical path difference at a certain reference position in the light scattering medium. The difference, which has thus been calculated, is then divided by the thickness of the light scattering medium. In this manner, a distribution of relative refractive index differences at different positions in the light scattering medium can be obtained.

The distribution of the refractive index differences in the light scattering medium is the distribution of the values, which are obtained from the spatial integration in the direction along which the light beam has passed through the light scattering medium. Therefore, as described above, at least either one of the light scattering medium and the entire system other than the light scattering medium or part of the entire system other than the light scattering medium may be moved by the movement means such that the light beam irradiated to the light scattering medium may be rotated and moved with respect to the light scattering medium. The operations described above are repeated at each position of rotation, and the information, which represents the distribution of the refractive index differences at respective positions of rotation, is thereby obtained. The obtained information, which represents the distribution of the refractive index differences at respective positions of rotation, is then reconstructed by the algorithms of the CT technique in the image reconstructing means. In this manner, a three-dimensional refractive index distribution image of the light scattering medium can be obtained.

As described above, with the first apparatus for obtaining refractive index distribution information of a light scattering medium in accordance with the present invention, the light beam, which has passed through the light scattering medium without being scattered, can be perfectly separated from the scattered light, which is radiated out of the light scattering medium. Therefore, only the light beam, which has passed through the light scattering medium without being scattered, can be detected with a high signal-to-noise ratio. Also, the distribution of large refractive index differences corresponding to optical path differences larger than the wavelength order can be measured quickly.

With the second apparatus for obtaining refractive index distribution information of a light scattering medium in accordance with the present invention, the coherent light beam is produced by the light source. The frequency of the coherent light beam is temporally swept by the modulation means. The light beam is then split by the optical system into the first light beam and the second light beam. The first light beam and the second light beam respectively travel along the first optical path and the second optical path, which have an optical path difference set in advance. Thereafter, the two light beams are combined with each other. Because an two optical paths have the optical path difference set in advance, the lengths of time required for the two light beams to travel respectively along the optical paths are different from each other. Because the frequency of the light beam, which has been produced by the light source, is swept temporally, at the time at which the two light beams having traveled respectively along the two optical paths are combined with each other, the frequencies of the two light beams take different values.

The light beam, which travels along the second optical path, merely travels along the optical path. On the other hand, the light beam, which travels along the first optical path, impinges upon the light scattering medium, which is located in the first optical path. As a result, a light beam which has passed through the light scattering medium without being scattered and scattered light are radiated out of the light scattering medium.

As described above, the optical path length of the light beam, which has passed through the light scattering medium without being scattered, and the optical path length of the cross talk light, which is among the scattered light, are different from each other.

Therefore, in cases where the length of the second optical path (i.e., the second optical path length) is longer than the length of the first optical path (i.e., the first optical path length), the difference between the first optical path length, that parses through the optical path of the light beam which has passed through the light scattering medium without being scattered and the second optical path length, becomes larger than the difference between the first optical path length, that passes through the optical path of the cross talk light and the second optical path length. Accordingly, at the time at which the two light beams are caused to interfere with each other by the optical system, the difference between the frequency of the light beam, which has passed through the light scattering medium without being scattered, and the frequency of the second light beam, which has traveled along the second optical path, takes a value larger than the difference between the frequency of the cross talk light and the frequency of the second light beam, which has traveled along the second optical path. The interference light generates a beat signal, which has the intensity repeatedly becoming high and low at a frequency equal to the difference between the frequencies of the two light beams before interfering with each other. Accordingly, the beat frequency of the interference light resulting from the interference of the light beam, which has passed through the light scattering medium without being scattered, and the second light beam becomes higher than the beat frequency of the interference light resulting from the interference of the cross talk light and the second light beam.

On the other hand, in cases where the length of the first optical path (i.e., the first optical path length) is longer than the length of the second optical path (i.e., the second optical path length), the difference between the first optical path length, that passes through the optical path of the light beam, which has passed through the light scattering medium without being scattered, and the second optical path length becomes smaller than the difference between the first optical path length, that passes through the optical path of the cross talk light, and the second optical path length. Accordingly, at the time at which the two light beams are caused to interfere with each other by the optical system, the difference between the frequency of the light beam, which has passed through the light scattering medium without being scattered, and the frequency of the second light beam, which has traveled along the second optical path, takes a value smaller than the difference between the frequency of the cross talk light and the frequency of the second light beam, which has traveled along the second optical path. Accordingly, the beat frequency of the interference light resulting from the interference of the light beam, which has passed through the light scattering medium without being scattered, and the second light beam becomes lower than the beat frequency of the interference light resulting from the interference of the cross talk light and the second light beam.

In accordance with the intensity of the interference light for each of the beat frequency, the interference light associated with the light beam, which has passed through the light scattering medium without being scattered and which has thus traveled along the optically shortest distance, can be discriminated from the interference light associated with the cross talk light. From the frequency of the discriminated interference light associated with the light beam, which has passed through the light scattering medium without being scattered and which has thus traveled along the optically shortest distance, a calculation is made to find the frequency equal to the difference between the frequency of the light beam, which has passed through the light scattering medium without being scattered, and the frequency of the light beam, which has traveled long the other optical path and which is caused to interfere with the light beam having passed through the light scattering medium without being scattered. Also, in accordance with the difference frequency thus calculated and the frequency sweep characteristics, a calculation is made to find the optical path difference between the optical path along which the light beam having passed through the light scattering medium without being scattered has traveled, and the optical path, along which the light beam caused to interfere with the light beam having passed through the light scattering medium without being scattered has traveled. This calculation is made for each of different positions in the light scattering medium. A calculation is then made to find the difference between the optical path difference at each of different positions in the light scattering medium and the optical path difference at a certain reference position in the light scattering medium. The difference, which has thus been calculated, is then divided by the thickness of the light scattering medium. In this manner, a distribution of relative refractive index differences at different positions in the light scattering medium can be obtained.

As in the first apparatus for obtaining refractive index distribution information of a light scattering medium in accordance with the present invention, the distribution of the refractive index differences in the light scattering medium is the distribution of the values, which are obtained from the spatial integration in the direction along which the light beam has passed through the light scattering medium. Therefore, as described above, at least either one of the light scattering medium and the entire system other than the light scattering medium of part of the entire system other than the light scattering medium may be moved by the movement means such that the light beam irradiated to the light scattering medium may be rotated and moved with respect to the light scattering medium. The operations described above are repeated at each position of rotation, and the information, which represents the distribution of the refractive index differences at respective positions of rotation, is thereby obtained. The obtained information, which represents the distribution of the refractive index differences at respective positions of rotation, is then reconstructed by the algorithms of the CT technique in the image reconstructing means. In this manner, a three-dimensional refractive index distribution image of the light scattering medium can be obtained.

As described above, with the second apparatus for obtaining refractive index distribution information of a light scattering medium in accordance with the present invention, the light beam, which has passed through the light scattering medium without being scattered, can be perfectly separated from the scattered light, which is radiated out of the light scattering medium. Therefore, only the light beam, which has passed through the light scattering medium without being scattered, can be detected with a high signal-to-noise ratio. Also, the distribution of large refractive index differences corresponding to optical path differences larger than the wavelength order can be measured quickly.

BRIEF DESCRIPTION OF THE DRAWINGS

FIG. 10 is a block diagram showing a different embodiment of the apparatus for obtaining refractive index distribution information of a light scattering medium in accordance with the present invention.

DESCRIPTION OF THE PREFERRED EMBODIMENTS

The present invention will hereinbelow be described in further detail with reference to the accompanying drawings.

Figure 1:
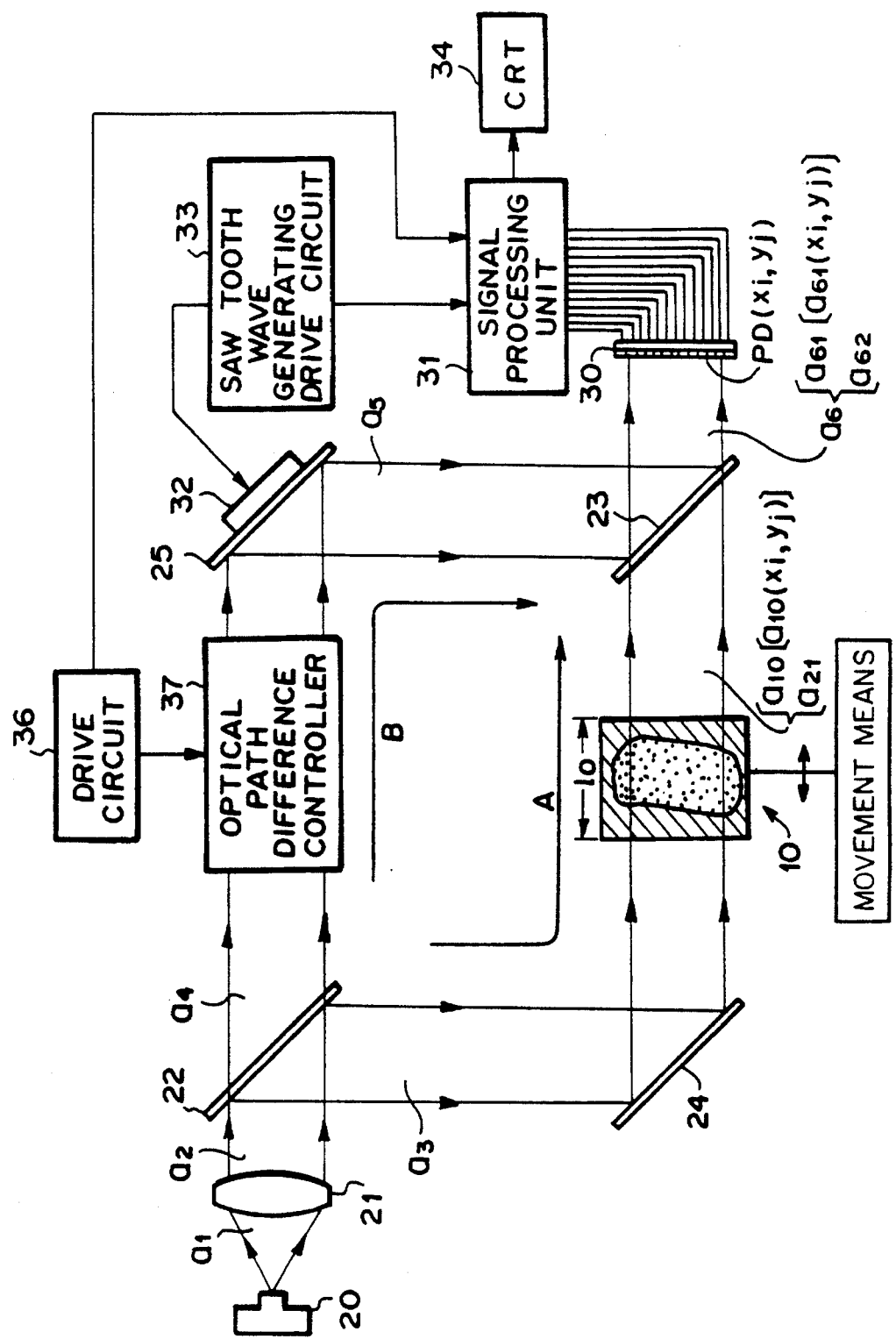
FIG. 1 is a block diagram showing a first embodiment of the apparatus for obtaining refractive index distribution information of a light scattering medium in accordance with the present invention.

FIG. 1 is a block diagram showing a first embodiment of the apparatus for obtaining refractive index distribution information of a light scattering medium in accordance with the present invention. The illustrated apparatus for obtaining refractive index distribution information comprises an SLD (super-luminescent diode) light source 20 for producing an SLD light beam al having a frequency ωO, and a collimator lens 21 for collimating the light beam a1, which has been produced by the SLD light source 20, into a collimated light beam a2. The apparatus for obtaining refractive index distribution information also comprises beam splitters 22, 23 and mirrors 24, 25 for splitting the light beam a2, which has been collimated by the collimator lens 21, into light beams a3 and a4, causing the light beams a3 and a4 to travel respectively along two optical paths A and B having approximately equal optical path lengths, and thereafter superposing the light beams a3 and a4 one upon the other. The apparatus for obtaining refractive index distribution information further comprises a piezo-electric device 32, which modulates the phase of the light beam a4 traveling among the optical path B in a saw tooth wave form shown in FIG. 2, and a saw tooth wave generating drive circuit 33 for generating a signal, which drives the piezo-electric device 32. The apparatus for obtaining refractive index distribution information still further comprises a photodetector 30 constituted of a two-dimensional array of a plurality of photodiodes PD(xi, yj), which detect the optical intensity of a light beam a6 obtained by superposing the light beams a3 and a4 one upon the other by the beam splitter 23, and which photoelectrically converts the detected optical intensity and feeds out an electric signal. The apparatus for obtaining refractive index distribution information also comprises a signal processing unit 31 for calculating the optical path difference between the optical paths, which the two light beams before being superposed one upon the other travel, from the optical intensities detected by the respective photodiodes PD(xi, yj) of the photodetector 30. The signal processing unit 31 also measures the distribution of refractive index differences in a light scattering medium 10 from the distribution of the optical path differences corresponding to the respective photodiodes PD(xi, yj).

The part (xi, yj) of PD(xi, yj) represents the position on the x-y coordinate system of the two-dimentional photo detecting surface of the photodetector 30. Therefore, PD(xi, yj) represents the photodiode, which is located at the position having the coordinates (xi, yj).

The light beam a2, which has been collimated by the collimator lens 21, is split by the beam splitter 22 into the light beams a3 and a4, which respectively travel along the two optical paths A and B. The phase of the light beam a4 is modulated by the piezo-electric device 32, and its frequency is thereby shifted. The light beam a4 will hereinbelow be referred to as the reference light beam a4 (or a5). An optical path difference controller 37, which modulates the optical path length of the optical path B and thereby controls the optical path difference between the optical path A and the optical path B, is located in the optical path B of the reference light a4. The optical path difference controller 37 is connected to a drive circuit 36, which generates a signal for driving the optical path difference controller 37.

Figure 6A:
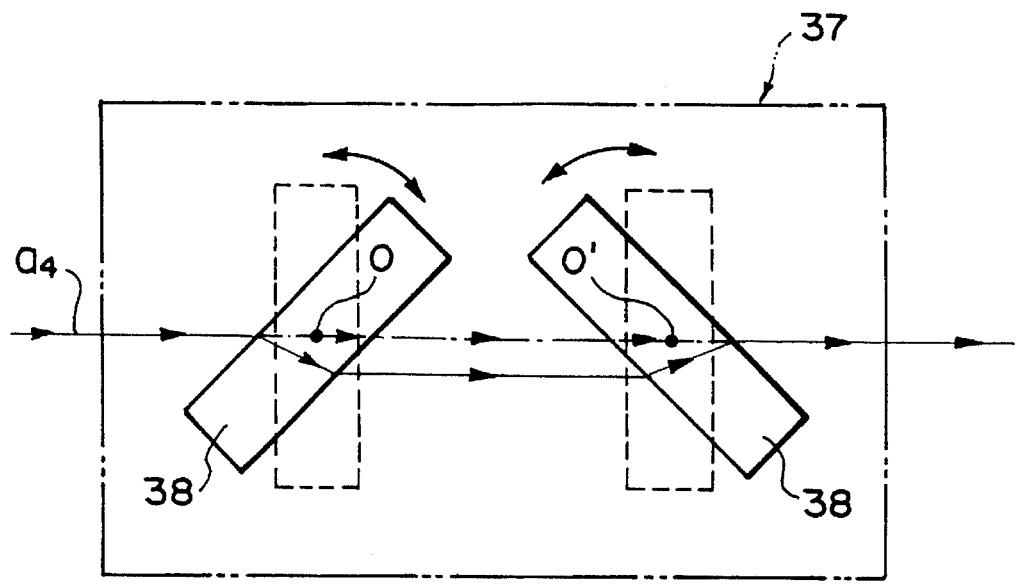
FIGS. 6A and 6B are schematic views showing examples of optical path difference controllers.
Figure 6B:
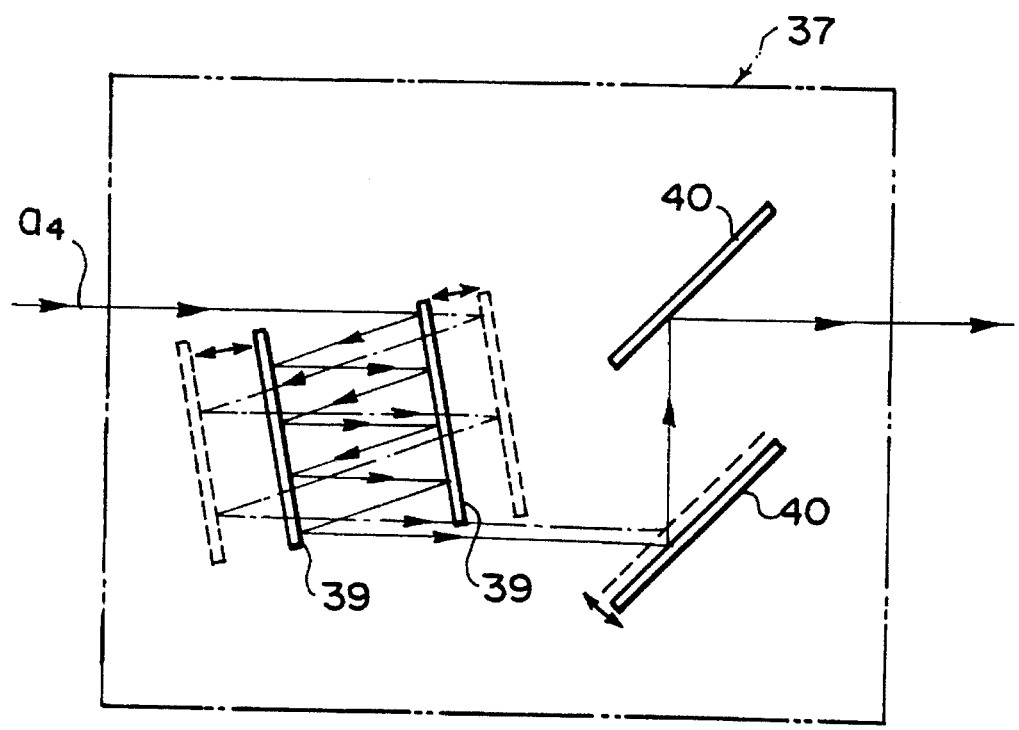

By way of example, as illustrated in FIG. 6A, the optical path difference controller 37 may be constituted of two light-permeable plates 38, 38, which are positioned facing each other and can be rotated by an identical angle in reverse directions around center points 0 and 0'. Alternatively, as illustrated in FIG. 6B, the optical path difference controller 37 may be constituted of two mirrors 39, 39, which stand facing each other and are inclined slightly with respect to the incident light, and which can be moved in parallel such that the distance between them can be varied.

Figure 3A:
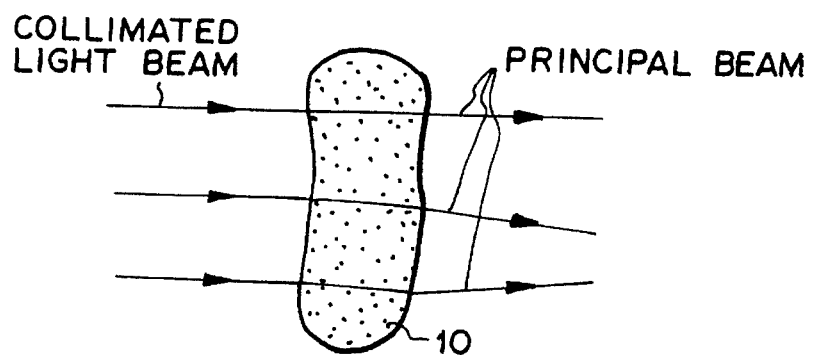
FIGS. 3A, 3B, and 3C are explanatory views showing how compensation is made for refraction of incident light and radiated light at boundaries of a light scattering medium.
Figure 3B:
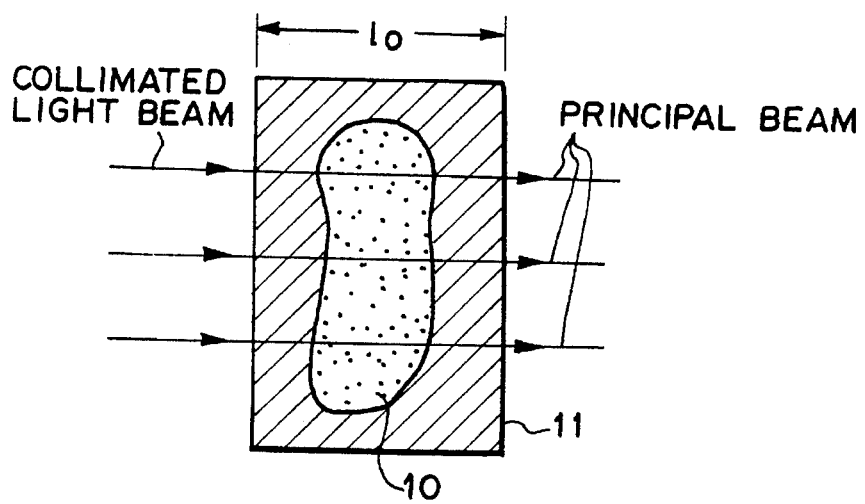
Figure 3C:
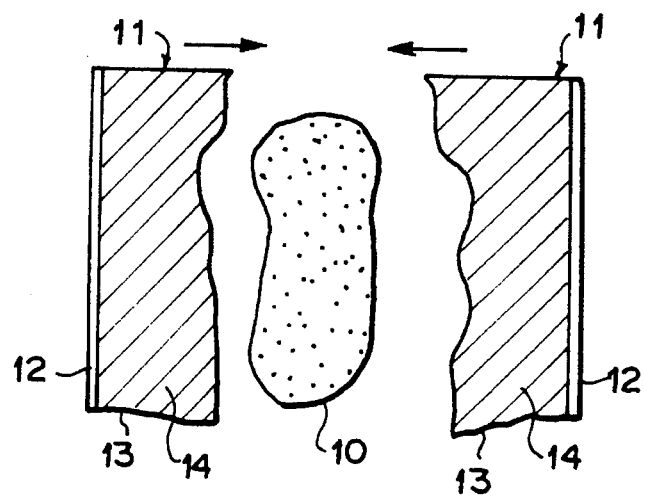

The light scattering medium 10, the refractive index distribution of which is to be measured, is located in the optical path A. The light scattering medium 10 has a thickness 1o in the direction along which the light beam a3 passes. As illustrated in FIG. 3A, the surface of the light scattering medium 10 has a curved shape. Therefore, when the light beam impinges upon the light scattering medium 10 and is radiated out of the light scattering medium 10, the light beam is refracted and the direction of travel of the principal beam changes. In such cases, an artifact is caused to occur. Therefore, as illustrated in FIG. 3B, a light-permeable matching medium 11, which has approximately the same refractive index as the refractive index of the light scattering medium 10, is located such that it may be in close contact with the light scattering medium 10. In this manner, the direction of travel of the principal beam is prevented from being changed. The light entry face and the light radiating face of the matching medium 11 are finished approximately normal to the direction of travel of the light beam. For example, as illustrated in FIG. 3C, the matching medium 11 may be constituted of flexible bag bodies 13, 13, which are made of very thin films, such as polyethylene films, and which are filled with a liquid medium 14 having the same refractive index as the refractive index of the light scattering medium 10, and plane-parallel glass plates 12, 12, which are respectively in close contact with the flexible bag bodies 13, 13. The flexible bag bodies 13, 13 are pushed against the light scattering medium 10 from the light entry side and the light radiating side so as to constitute a sandwich structure.

As an aid in facilitating the explanation, the combination of the light scattering medium 10 and the matching medium 11 will hereinbelow be referred to as the light scattering medium 10.

How this embodiment operates will be described hereinbelow.

Figure 4A:
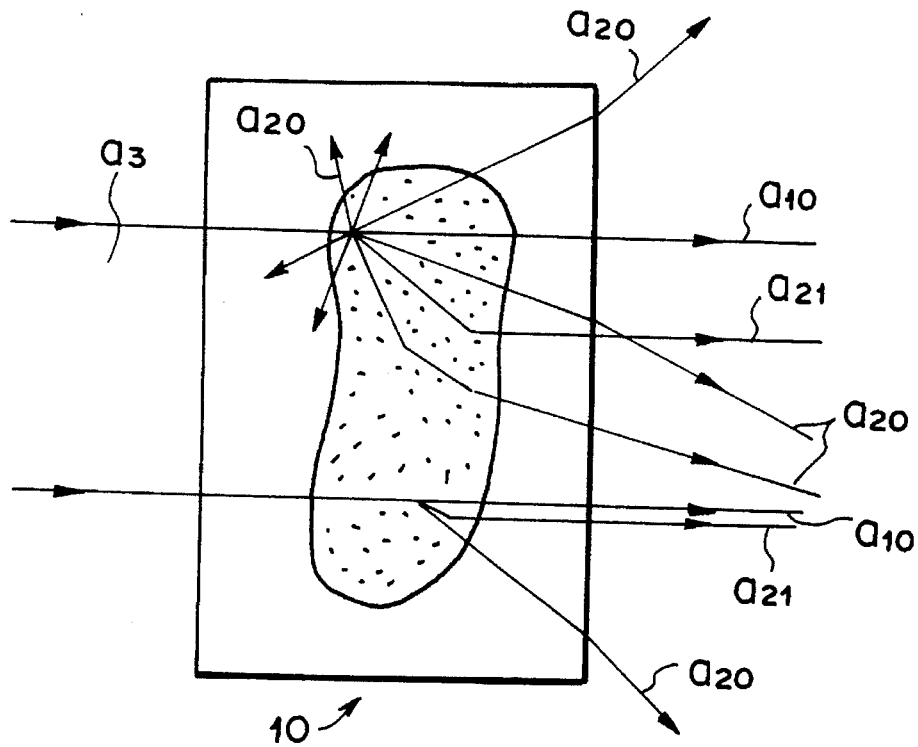
FIG. 4A is an explanatory view showing the relationship between a light beam, which has passed through a light scattering medium without being scattered, and cross talk light.

The SLD light beam al, which has been produced by the light source 20, is collimated by the collimator lens 21 into the collimated light beam a2. The collimated light beam a2 is split by the beam splitter 22 into two light beams a3 and a4, which travel respectively along the two optical paths A and B. As illustrated in FIG. 4A, the light beam a3, which travels along the optical path A, impinges upon the light scattering medium 10 and is divided into scattered light a20 and a light beam a10, when has passed through the light scattering medium 10 without being scattered. The scattered light a20 is scattered by the light scattering substance in the region inside of the light scattering medium 10 towards various directions and is thereby radiated out of the light scattering medium 10. The light beam a10, which has passed through the light scattering medium 10 without being scattered, carries the refractive index information of the light scattering medium 10 and is radiated out of the light scattering medium 10 in the same direction as the incidence direction. As illustrated in FIG. 4A, due to multiple scattering, or the like, part of the scattered light a20 is radiated out of the light scattering medium 10 in the same direction as the direction along which the light beam a10 (having passed through the light scattering medium 10 without being scattered) is radiated out. Such part of the scattered light a20 will hereinbelow be referred to as the cross talk light.

The cross talk light a21 has the characteristic that, due to the multiple scattering in the region inside of the light scattering medium 10, it travels along an optical path having an optical path length longer than the optical path length by which the light beam a10 (passing through the light Scattering medium 10 without being scattered) travels in the region inside of the light scattering medium 10.

Figure 4B:
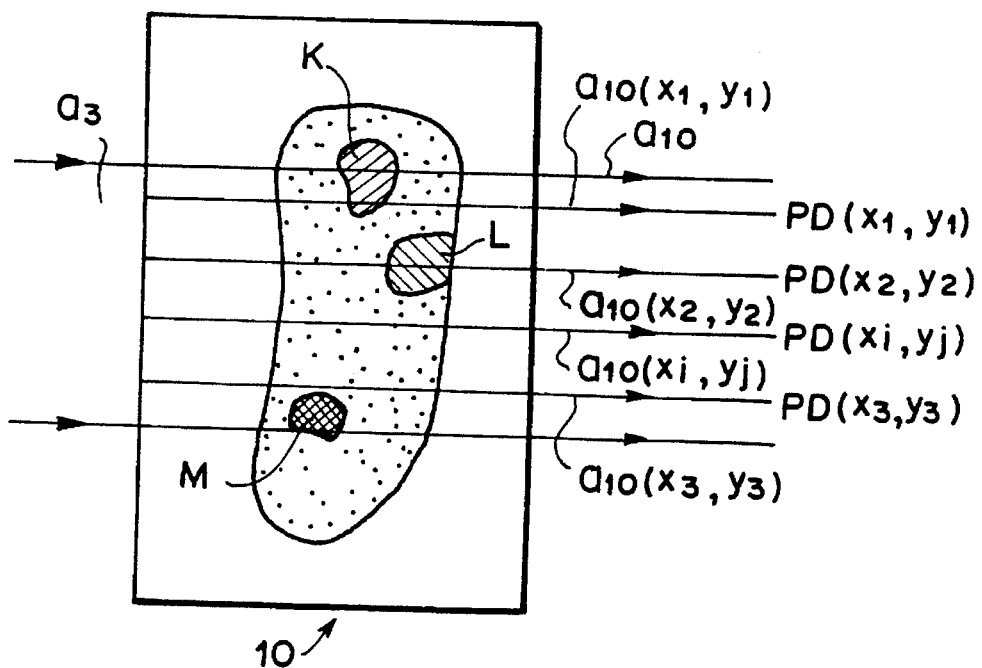
FIG. 4B is an explanatory view showing how a refractive index distribution is obtained with a light beam, which has passed through a light scattering medium without being scattered.

On the other hand, as illustrated in FIG. 4B, the light beam a10, which has passed through the light scattering medium 10 without being scattered, is composed of light a10(xi, yj), which has passed through each of portions of the light scattering medium 10 having the coordinates (xi, yJ) on the x-y coordinate system that is normal to the light beam a10, which has passed through the light scattering medium 10 without being scattered. The light a10(xi, yj), which passes through the light scattering medium 10 without being scattered, travels by the optical path length corresponding to the refractive index in the optical path in the region inside of the light scattering medium 10 and is then radiated out of the light scattering medium 10. The light a10(xi, yj), which has passed through the light scattering medium 10 without being scattered, impinges upon the photodiode PD(xi, yj), which is located at the position having the corresponding coordinates (xi, yj).

For example, in FIG. 4B, regions K, L, and M have refractive indexes different from the refractive index of the major part of the light scattering medium 10. The light a10(xl, yl), which passes through the light scattering medium 10 without being scattered, passes through the region K and is then radiated out of the light scattering medium 10. The light a10(x2, y2), which passes through the light scattering medium 10 without being scattered, passes through the region L having a different refractive index and is then radiated out of the light scattering medium 10. Also, the light a10(x3, y3), which passes through the light scattering medium 10 without being scattered, passes through the region M having a different refractive index and is then radiated out of the light scattering medium 10.

Figure 2:
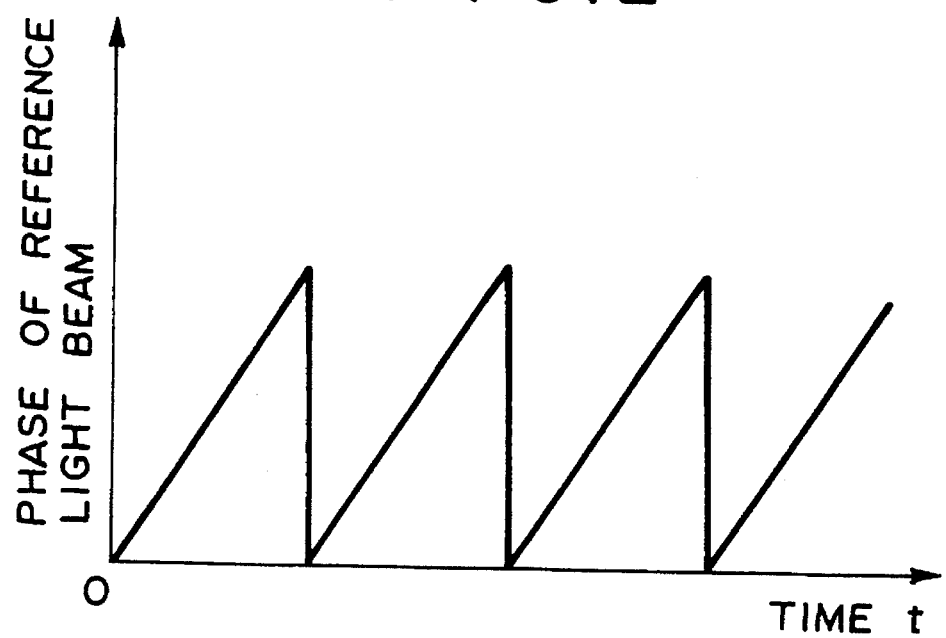
FIG. 2 is a graph showing a phase sweep wave form of reference light.

On the other hand, the phase of the light beam a4, which travels along the other optical path B, is swept in the saw tooth wave form shown in FIG. 2 by the mirror 25, which is driven together with the piezo-electric device 32 driven by the saw tooth wave generating drive circuit 33. In this manner, the light beam a4 is converted into the reference light beam a5 having a frequency $\omega 1$, which is not equal to $\omega 0$ The reference light beam a5 thus obtained and the light a10(xi,yj), which has passed through the light scattering medium 10 without being scattered, are combined with each other by the beam splitter 23. Also, the reference light beam a5 and the cross talk light a21, which has been radiated out of the light scattering medium 10, are combined with each other by the beam splitter 23. The optical intensity of the combined light beam is detected by the photodetector 30, photoelectrically converted into an electric signal proportional to the optical intensity, and fed into the signal processing unit 31.

The coherence length of the SLD light beam a1 falls within the range of 40 μm to 50 μm and is thus very short in wavelength. Therefore, if the optical path difference between the optical path A and the optical path B is not equal to approximately zero, the light beams having traveled along the optical path A and the optical path B will not interfere with each other when they are combined with each other. When the optical path difference between the optical path A and the optical path B is set to be approximately equal to zero by the optical path difference controller 37, which is driven by the drive circuit the reference light beam a5 and the light a10(xi, yj), which has passed through the light scattering medium 10 without being scattered, are caused to interfere with each other in accordance with the optical path difference. Alternatively, the reference light beam a5 and the cross talk light a21 are caused to interfere with each other in accordance with the optical path difference. The light beam a6 obtained from the interference generates a beat signal, which has an intensity repeatedly becoming high and low at a frequency $\Delta\omega(=|\omega 0-\omega 1|)$ equal to the difference between the frequencies of the two light beams before interfering with each other. Specifically, as described above, the interference between the light a10(xi, yj), which has passed through the light scattering medium 10 without being scattered, and the reference light beam a5 or the interference between the cross talk light a21 and the reference light beam a5 occurs in accordance with the optical path difference. The light obtained from the former interference will hereinbelow be referred to as interference light a61(Xi, Yj). The light obtained from the latter interference will hereinbelow be referred to as interference light a62.

Figure 5:
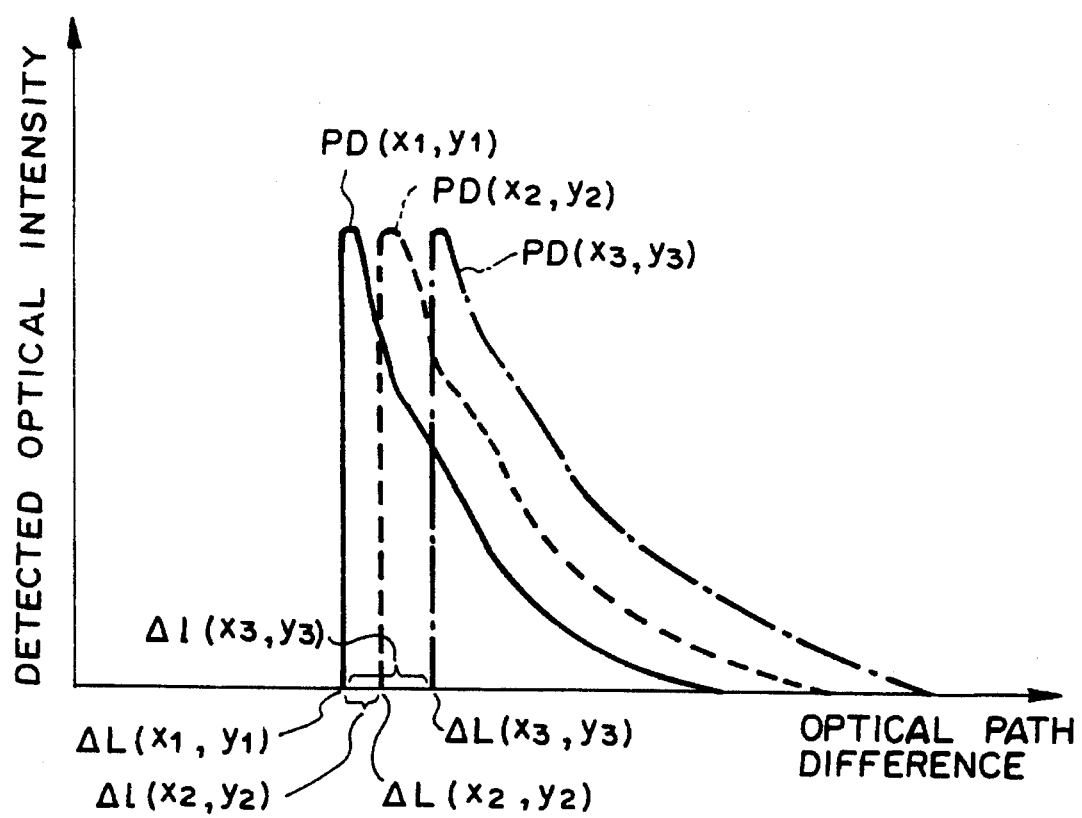
FIG. 5 is a graph showing the relationship between an optical path difference and an optical intensity of interference light.

As illustrated in FIG. 4B, the interference light a61(xi, yj) obtained from the interference between the light a10(xi, yj), which has passed through the light scattering medium 10 without being scattered, and the reference light beam a5, and the interference light a62 obtained from the interference between the cross talk light a21 and the reference light beam a5 impinge upon the photodiodes PD(xi, yj) of the photodetector 30 corresponding to the coordinates (xi, yj). The optical intensities of the interference light a61(xi, yj) and the interference light a62 are respectively detected by the photodiodes PD(xi, yj). FIG. 5 shows the detected optical intensity with respect to the optical optical-path difference $\Delta L$, which has been detected by the optical path difference controller 37. By way of example, FIG. 5 shows the optical intensities detected by the photodiodes PD(x1, y1), PD(x2, y2), and PD(x3, y3). As for the illustrated detected optical intensity curves, for example, the optical path difference $\Delta L(x1, y1)$, at which the optical intensity detected by the photodiode PD(xl, yl) rises characteristically, represents the optical path difference occurring when the interference light a61(x1, y1) obtained from the interference between the light a10(x1, y1), which has passed through the light scattering medium 10 without being scattered, and the reference light beam a5 is detected. The optical path difference corresponding to the part of the detected optical intensity curve, at which the detected optical intensity decreases little by little, represents the optical path difference of the interference light a62 associated with the cross talk light a21.

The signal processing unit 31 detects the optical path differences ΔL(xi, yj), at which the optical intensities rise characteristically, from the optical intensities detected by the respective photodiodes PD(xi, yj). The signal processing unit 31 then calculates the differences ΔL(xi, yj) between the optical path differences ΔL(xi, yj) and the optical path difference ΔL(x1, y1) at the position having the coordinates (x1, y1). The differences Δl(xi, yj) are then divided by the physical thickness lo taken in the direction along which the light beam passes through the light scattering medium 10. The values obtained from the division represent the values which correspond to the refractive indexes at the positions having the coordinates (xi, yj), with respect to the value which corresponds to the refractive index at the position having the coordinates (x1, y1) in the light scattering medium 10 and which is taken as the reference. By the calculation of such values, it is possible to obtain the distribution of the refractive index differences in the light scattering medium 10.

In the manner described above, the information representing the distribution of the refractive index differences at the portions having the coordinates (xi, yj) in the light scattering medium 10 is obtained from the signal processing unit 31. The obtained information is then fed into a cathode ray tube (CRT) display device 34 and is displayed thereon as an image representing the distribution of the refractive index differences in the light scattering medium 10.

As described above, with this embodiment of the apparatus for obtaining refractive index distribution information of a light scattering medium in accordance with the present invention, the light beam, which has passed through the light scattering medium without being scattered, and scattered light, which is radiated out of the light scattering medium, can be easily separated from each other. As a result, the refractive index distribution information of the light scattering medium can be detected with a high signal-to-noise ratio.

Figure 7:
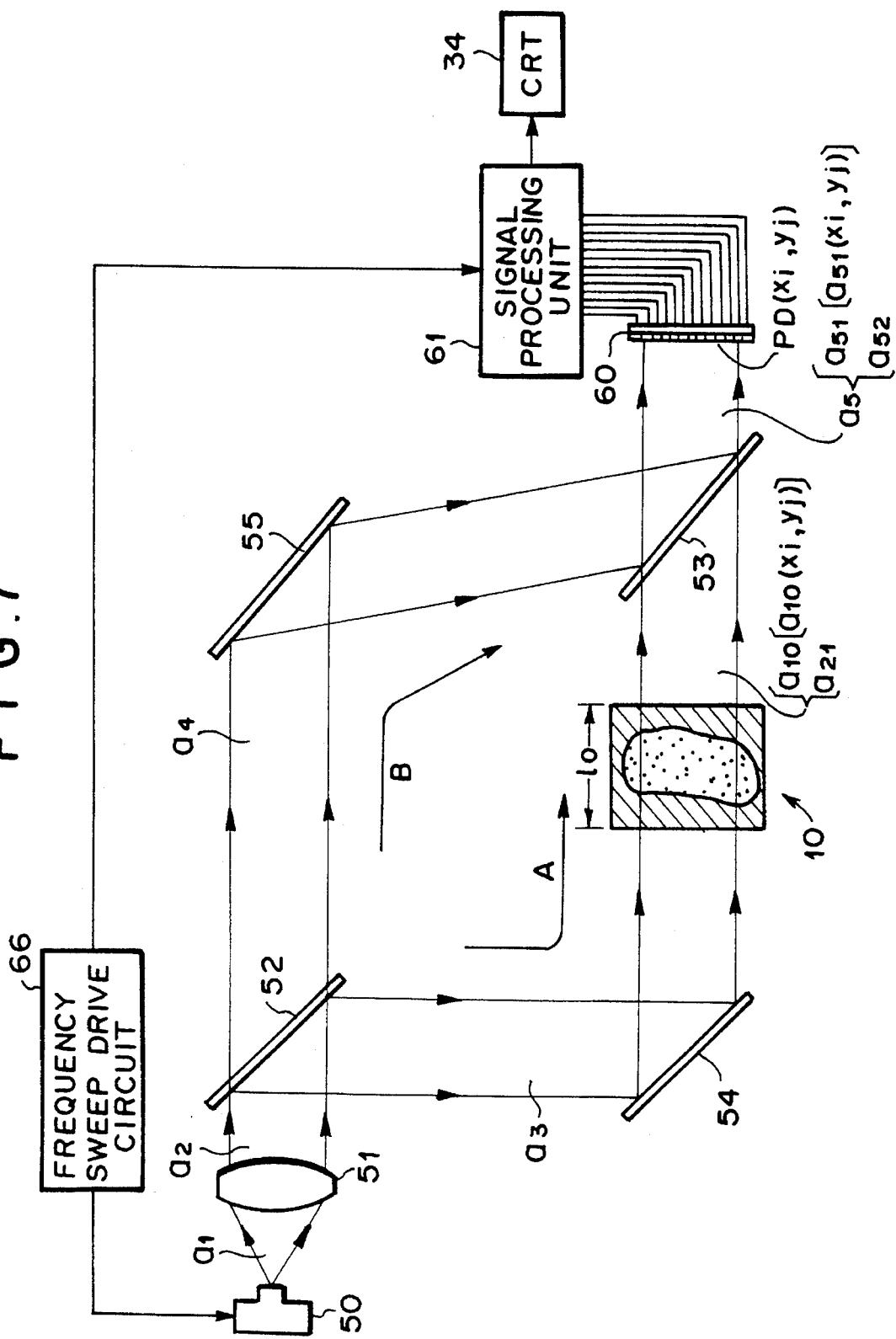
FIG. 7 is a block diagram showing a second embodiment of the apparatus for obtaining refractive index distribution information of a light scattering medium in accordance with the present invention.
Figure 8:
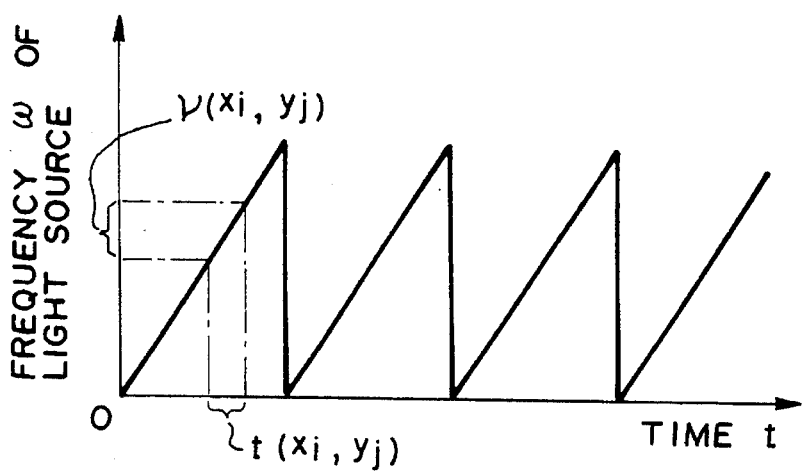
FIG. 8 is a graph showing a frequency sweep wave form of a laser beam produced by a light source.

In this embodiment of the apparatus or obtaining refractive index distribution information of a light scattering medium in accordance with the present invention, the optical path difference controller 37, the piezo-electric device 32, and the saw tooth wave generating drive circuit 33 are located in the optical path B, which is different from the optical path A in which the light scattering medium 10 is located. The apparatus for obtaining refractive index distribution information of a light scattering medium in accordance with the present invention is not limited to the embodiment described above and may be embodied in different ways such that the elements described above may be located in the optical path A, in which the light scattering medium 10 is located, or may be respectively distributed to both of the optical paths A and FIG. 7 is a block diagram showing a second embodiment of the apparatus for obtaining refractive index distribution information of a light scattering medium in accordance with the present invention. The illustrated apparatus for obtaining refractive index distribution information comprises a laser beam source for producing a laser beam a1, and a frequency sweep drive circuit 66 or sweeping the frequency of the laser beam a1 in the saw tooth wave form shown in FIG. 8. The apparatus for obtaining refractive index distribution information also comprises a collimator lens 51 collimating the laser beam a1, which has been produced by the laser beam source 50 and the frequency of which has been swept by the frequency sweep drive circuit 66, into a collimated laser beam a2. The apparatus for obtaining refractive index distribution information further comprises beam splitters 52, 53 and mirrors 54, 55 for splitting the collimated laser beam a2 into two laser beams a3 and a4, causing the laser beams a3 and 84 to travel respectively along two optical paths A ad having slightly different optical path lengths, and thereafter superposing the laser beams a3 and a4 one upon the other. The apparatus for obtaining refractive index distribution information still comprises a photodetector 60 constituted of a two-dimensional array of a plurality of photodiodes PD(xi, yJ), which detect the optical intensity of a laser beam a5 obtained by superposing the laser beams a3 an a4 one upon the other by the beam splitter 53, and which photoelectrically converts the detected optical intensity and feeds out an electric signal. The apparatus for obtaining refractive index distribution information also comprises a signal processing unit 61 for detecting the difference frequency, which is equal to the difference between the frequencies of the two interfering laser beams, from the frequencies of change in the optical intensities detected by the respective photodiodes PD(xi, yj) of the photodetector 60. The signal processing unit 61 also calculates the distribution of relative refractive index differences at different positions in a light scattering medium 10 from the detected difference frequency and the frequency sweep characteristics of the frequency sweep drive circuit 66.

The laser beam a2, which has been collimated by he collimator lens 51, is split by the beam splitter 52 into the laser beams a3 and a4, which respectively travel along the two optical paths A and S. The light scattering medium 10, the refractive index distribution of which is to be measured, is located in the optical path A. As in the first embodiment described above, the light scattering medium 10 is covered by the matching medium 11.

How the second embodiment operates will be described hereinbelow.

As described above, the laser beam a1 is produced by the laser beam source 50. The frequency of the laser beam a1 is temporally swept by the frequency sweep drive circuit 66 in the form shown in FIG. 8. The laser beam a1, which has been produced by the laser beam source 50 and the frequency of which has been swept, is collimated by the collimator lens 51 into the collimated laser beam a2. The collimated laser beam a2 is split by the beam splitter 52 into two laser beams a3 and a4, which travel respectively along the two optical paths A and B. The laser beam 3, which travels along the optical path A, impinges upon the light scattering medium 10. As explained above in the first embodiment, the laser beam a3 is radiated out of the light scattering medium 10 as a laser beam a10, which has linearly passed the shortest distance through the light scattering medium 10 without being scattered, and as the cross talk light a21, which travels along an optical path having an optical path length longer than the optical path length of the laser beam a10, which has passed through the light scattering medium 10 without being scattered.

Of the laser beam a3, which has traveled along the optical path A, the laser beam a1O, which has passed through the light scattering medium 10 without being scattered, and the cross talk light a21 are respectively combined by the beam splitter 53 with the laser beam a4, which has traveled along the other optical path B. In this manner, the laser beam a10 and the cross talk light a21 are respectively caused to interfere with the laser beam a4.

The time required for the laser beam a10, which passes through the light scattering medium 10 without being scattered, to arrive at the beam splitter 53 is shorter than the time required for the cross talk light a21 to arrive at the beam splitter 53. Therefore, the frequency of the laser beam a4 interfering with the laser beam a10, which has passed through the light scattering medium 10 without being scattered, on the beam splitter 53 is lower than the frequency of the laser beam a4 interfering with the cross talk light a21 on the beam splitter 53. Accordingly, for example, in cases where the length of the optical path B is shorter than the length of the optical path A, the difference between the frequency of the laser beam a4 interfering with the laser beam a10, and the frequency of the laser beam a10, itself becomes smaller than the difference between the frequency of the laser beam a4 interfering with the cross talk light a21 and the frequency of the cross talk light a21. As a result, the frequency of the beat signal occurring in interference light a51, that is associated with the laser beam a10, which has passed through the light scattering medium 10 without being scattered, becomes lower than the frequency of the beat signal occurring in interference light a52, that is associated with the cross talk light a21.

On the other hand, in cases where the length of the optical path B is longer than the length of the optical path A, the difference between the frequency of the laser beam a4 interfering with the laser beam a10, and the frequency of the laser beam a10, itself becomes larger than the difference between the frequency of the laser beam a4 interfering with the gross talk light a21 and the frequency of the cross talk light a21. As a result, the frequency o the beat signal occurring in the interference light a51, that is associated with the laser beam a10, which has passed through the light scattering medium 10 without being scattered, becomes higher than the frequency of the beat signal occurring in the interference light a52, that is associated with the cross talk light a21.

As described above, the laser beam a10, which has passed through the light scattering medium 10 without being scattered, and the cross talk light a21 can be discriminated from each other in accordance with the frequency of the beat signal occurring due to the interference.

As in the first embodiment described above, the laser beam a10, which has passed through the light scattering medium 10 without being scattered, is composed of light a10(xi, yj), which has passed through each portions of the light scattering medium 10 having the coordinates (xi, yj) on the x-y coordinate system that is normal to the laser beam a10 The light a18(xi, yj), which passes through the light scattering medium 10 without being scattered, travels by the optical path length corresponding to the refractive index in the optical path in the region inside of the light scattering medium 10 and is then radiated out the light scattering medium 10. The light a10(xi, yj), which has passed through the light scattering medium 10 without being scattered, impinges upon the photodiode PD(xi, yj), which is located at the position having the corresponding coordinates (xi, yj).

Figure 9:
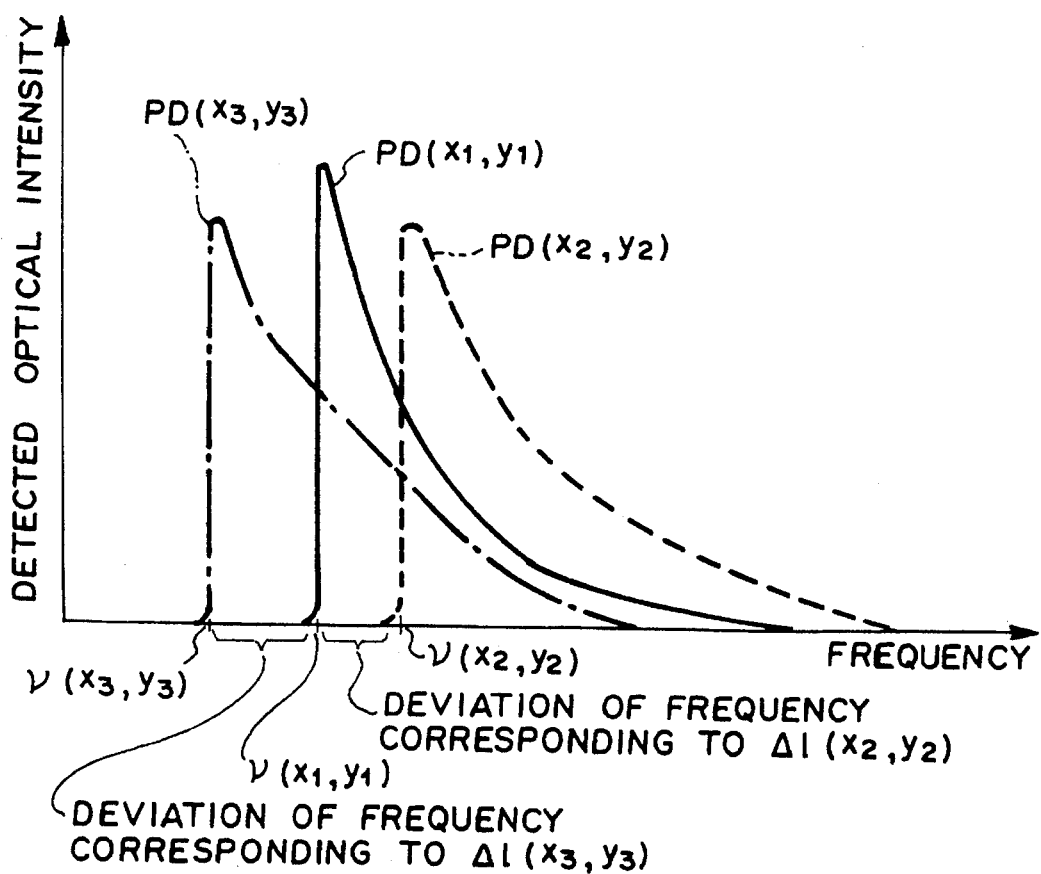
FIG. 9 is a graph showing the relationship between a beat frequency and an optical intensity of interference light.

Of the optical intensity curves detected by the photodiodes PD(xi, yj), those detected by the photodiodes PD(x1, y1), PD(x2, y2), and PD(x3, y3) are shown in FIG. 9. As for the illustrated detected optical intensity curves, for example, the frequency v(x1, y1), at which the optical intensity detected by the photodiode PD(x1, y1) rises characteristically, represents the frequency of the interference light a51(x1, y1) obtained from the interference between the light a10(x1, y1), which has passed through the light scattering medium 10 without being scattered, and the reference laser beam a5. The frequency corresponding to the part of the detected optical intensity curve, at which the detected optical intensity decreases little by little, represents the frequency of the interference light a52 associated with the cross talk light a21.

The signal processing unit 61 detects the frequencies v(xi, yj), at which the optical intensities rise characteristically, from the optical intensities detected by the respective photodiodes PD(xi, yj). The frequency of the beat signal of the interference light is the difference between the frequencies of the two light beams before interfering with each other. Therefore, from the frequencies v(xi, yj), at which the optical intensities rise characteristically, and the frequency sweep characteristics of the frequency sweep drive circuit 66 shown in FIG. 8, a calculation is made to find the difference t(xi, yj) between the optical path passage time off the light a10(xi, yj), which has passed through the light scattering medium 10 without being scattered, and the optical path passage time of the reference laser beam a5. Also, also the optical-path difference ΔL'(xi, yj) corresponding to the time difference (xi, yj) is calculated. The optical-path difference ΔL'(xi, yj) is the optical-path difference and varies in accordance with the refractive index of the portion having the coordinates (xi, yj) in the light scattering medium 10.

The signal processing unit 61 then calculates the differences Δ1(xi, yj) between the optical optical-path differences ΔL'(xi, yj) and the optical-path difference ΔL'(x1, y1) at the position having the coordinates (x1, y1). The differences Δ1(xi, yj) are then divided by the physical thickness lo taken in the direction, along which the laser beam passes through the light scattering medium 10. In this manner, the refractive index differences at the portions having the coordinates (xi, yj) in the light scattering medium 10 are calculated.

In the manner described above, the information representing the distribution of the refractive index differences at the portions having the coordinates (xi, yj) in the light scattering medium 10 is obtained from the signal processing unit 61. The obtained information is then fed into the CRT display device 34 and is displayed thereon as an image representing the distribution of the refractive index differences in the light scattering medium 10.

As described above, with the second embodiment of the apparatus for obtaining refractive index distribution information of a light scattering medium in accordance with the present invention, the laser beam, which has passed through the light scattering medium without being scattered, and scattered light, which is radiated out of the light scattering medium, can be easily separated from each other. As a result, the refractive index distribution information of the light scattering medium can be detected with a high signal-to-noise ratio.

In the first and second embodiments of the apparatus for obtaining refractive index distribution information of a light scattering medium in accordance with the present invention, it may occur that the amount of the scattered light component is larger than the light component, which has passed through the light scattering medium 10 without being scattered. Also, it may occur that the detected optical intensity curves shown in FIG. 9 extend over wide frequency bands. In such cases, for example, in the second embodiment, it becomes difficult to detect the frequency v(xi, yj) of the interference light a51(xi, yj) obtained from the interference between the light a10(xi, yj), which has passed through the light scattering medium 10 without being scattered, and the reference laser beam a5. In order to eliminate such problems, as illustrated in FIG. 10, the signal processing unit 31 in the first embodiment may be provided with a cross correlation processing unit 70. (Also, the signal processing unit 61 in the second embodiment may be provided with the cross correlation processing unit 70.) For example, with the cross correlation processing unit 70 connected to the signal processing unit 61, the detection of the frequency v(xi, yj) may be carried out by taking the frequency v(x1, y1) of the interference light a51(x1, y1), which has been detected at a point having the coordinates (x1, y1) in the light scattering medium 10, as a reference and carrying out calculations for cross correlation with other signals.

What is claimed is:

1. An apparatus for obtaining refractive index distribution information of a light scattering medium, comprising:

a light source for producing a low coherence light beam;

an optical system for splitting said low coherence light beam produced by said light source into a first light beam and a second light beam, said light beams traveling along a first and a second optical path, respectively, said optical paths being approximately equal in length, said optical system combining said first and second lights beams into a combined light beam thereafter, wherein said combined light beam comprises a scattered combined light beam and an unscattered combined light beam, said scattered combined light beam comprising a combination of said first light beam and a scattered portion of said second light beam passed through a light scattering medium therein;

said unscattered combined light beam comprising a combination of said first light beam and an unscattered portion of said second light beam passed through a light scattering medium therein;

a frequency shifter located along said first optical path for shifting a frequency of said first light beam so that respective frequencies of said first and said second light beam are approximately equal;

an optical path difference controller located along said first optical path for changing the length of said first optical path;

a photodetector comprising a one-dimensional or a two-dimentional array comprising a plurality of photo detecting devices thereof, said arrays being located along a plane situated orthogonal to a direction of said combined light beam, said photodetector for detecting the intensities of said scattered combined light beam and said unscattered combined light beam;

an operation means for:
   (a) detecting an optical path difference for said unscattered combined light beam representing a path difference between said first light beam and said unscattered portion of said second light beam;
   (b) calculating a difference between said path difference and a predetermined reference path difference;
   (c) dividing said calculated difference value by the thickness of said light scattering medium,
   thereby calculating a refractive index associated with each of the different positions of said light scattering medium.

2. An apparatus as defined in claim 1 wherein said low coherence light beam is a light beam produced by a superluminescent diode.

3. An apparatus as defined in claim 1 wherein said light scattering medium is covered with a light-permeable medium, said light-permeable medium having approximately the same refractive index as the refractive index of said light scattering medium, said light-permeable medium having a light entry face and a light radiating face, both of said faces finished to be normal to the direction of travel of said second light beam.

4. An apparatus as defined in claim wherein said photodetector is a one-dimensional photodetector, and the apparatus further comprises a scanning means for scanning at least either one of the one-dimensional photodetector and the system other than the one-dimensional photodetector in a direction, which is approximately normal to the direction along which the one-dimensional photodetector extends.

5. An apparatus as defined in claim 1 further comprising a movement means for moving either said light scattering medium or said optical system such that said second light beam may be rotated and moved with respect to said light scattering medium, and an image reconstructing means which forms a three-dimensional refractive index distribution image from refractive index distribution information obtained at each position of rotation.

6. An apparatus for obtaining refractive index distribution information of a light scattering medium, comprising:

a light source for producing a low coherence light beam;

a modulation means for temporally sweeping the frequency of said coherent light beam;

an optical system for splitting said low coherence light beam swept by said modulation means into a first light beam and a second light beam, said light beams traveling along a first and a second optical path, respectively, said optical paths being approximately equal in length, said optical system combining said first and second lights beams into a combined light beam thereafter, wherein said combined light beam comprises a scattered combined light beam and an unscattered combined light beam, said scattered combined light beam comprising a combination of said first light beam and a scattered portion of said second light beam passed through a light scattering medium therein;

said unscattered combined light beam comprising a combination of said first light beam and an unscattered portion of said second light beam passed through a light scattering medium therein;

a frequency shifter located along said first optical path for shifting a frequency of said first light beam so that respective frequencies of said first and said second light beam are approximately equal;

an optical path difference controller located along said first optical path for changing the length of said first optical path;

a photodetector comprising a one-dimensional or a two-dimentional array comprising a plurality of photo detecting devices thereof, said arrays being located along a plane situated orthogonal to a direction of said combined light beam, said photodetector for detecting the intensities of said scattered combined light beam and said unscattered combined light beam;

an operation means for:
   (a) detecting an optical path difference for said unscattered combined light beam representing a path difference between said first light beam and said unscattered portion of said second light beam;
   (b) calculating a difference between said path difference and a predetermined reference path difference;

(c) dividing said calculated difference value by the thickness of said light scattering medium, thereby calculating a refractive index associated with each of the different positions of said light scattering medium.

7. An apparatus as defined in claim 6 wherein said light source for producing said coherent light beam also serves as said modulation means for temporally sweeping the frequency of said coherent light beam produced by said light source.

8. An apparatus as defined in claim 6 wherein said light scattering medium is covered with a light-permeable medium, said light-permeable medium having approximately the same refractive index as the refractive index of said light scattering medium, said light-permeable having a light entry face and a light radiating face, both of said faces finished to be normal to the direction of travel of said second light beam.

9. An apparatus as defined in claim 6 wherein said photodetector is a one-dimensional photodetector, and the apparatus further comprises:

a scanning means for scanning at least either one of the one-dimensional photodetector and the system other than the one-dimensional photodetector in a direction, which is approximately normal to the direction along which the one-dimensional photodetector extends.

10. An apparatus as defined in claim 6 further comprising a movement means for moving either said light scattering medium or said optical system such that said second light beam may be rotated and moved with respect to said light scattering medium, and an image reconstructing means which forms a three-dimensional refractive index distribution image from refractive index distribution information obtained at each position of rotation.

* * * * *